(12) United States Patent
Wells et al.

(10) Patent No.: US 7,655,425 B2
(45) Date of Patent: Feb. 2, 2010

(54) USES OF A CHEMOKINE RECEPTOR ABLE TO BIND TO MCP-1, MIP-1α AND/OR RANTES

(75) Inventors: Timothy N. C. Wells, Geneva (CH); Christine A. Power, Geneva (CH)

(73) Assignee: Glaxo Group Limited, Greenford Middlesex (GB)

( * ) Notice: Subject to any disclaimer, the term of this patent is extended or adjusted under 35 U.S.C. 154(b) by 458 days.

(21) Appl. No.: 10/933,356

(22) Filed: Sep. 3, 2004

(65) Prior Publication Data

US 2005/0014695 A1 Jan. 20, 2005

Related U.S. Application Data

(63) Continuation of application No. 09/764,413, filed on Jan. 19, 2001, now Pat. No. 6,919,432, which is a continuation of application No. 09/614,256, filed on Jul. 12, 2000, now abandoned, which is a continuation of application No. 08/875,573, filed as application No. PCT/GB96/00143 on Jan. 24, 1996, now Pat. No. 6,150,132.

(30) Foreign Application Priority Data

Jan. 27, 1995 (GB) .................................. 9501683.8

(51) Int. Cl.
G01N 33/567 (2006.01)
A61K 39/395 (2006.01)
C07K 14/715 (2006.01)

(52) U.S. Cl. .................... 435/7.21; 436/503; 424/145.1; 514/12

(58) Field of Classification Search ........................ None
See application file for complete search history.

(56) References Cited

U.S. PATENT DOCUMENTS

| | | | |
|---|---|---|---|
| 5,011,912 A | 4/1991 | Hopp et al. | |
| 6,150,132 A | 11/2000 | Wells et al. | |
| 6,919,432 B2 | 7/2005 | Wells et al. | |
| 2002/0160015 A1 | 10/2002 | Wells et al. | |

FOREIGN PATENT DOCUMENTS

| | | |
|---|---|---|
| EP | 0805859 B1 | 4/2005 |
| WO | WO 92/20372 | 11/1992 |
| WO | WO 94/07521 | 4/1994 |
| WO | WO 94/11504 | 5/1994 |
| WO | WO 94/21277 | 9/1994 |
| WO | WO 94/29348 | 12/1994 |

OTHER PUBLICATIONS

Elliot Marshall, Science, Mar. 2006. vol. 311, pp. 1688-1689.*
Conroy et al, Journal of Leukocyte Biology, 2003. vol. 74, pp. 558-563.*
Charo and Ransohoffds, New England Journal of Medicine, 2006, vol. 354, No. 6, pp. 610-621.*
Bischoff et al. "RANTES and related chemokines activate human basophil granulocytes through different G protein-coupled receptors" Eur. J. Immunol. 23:761-767 (1993).
Charo, et al. "Molecular cloning and functional expression of two monocyte chemoattractant protein 1 receptors reveals alternative splicing of the carboxyl-terminal tails" Proc. Natl. Acad. Sci. USA 91:2752-2756 (1994).
Chvatchko et al. "A key role for CC chemokine receptor 4 in lipopolysaccharide-induced endotoxic shock" J. Exp Med. 191:1755-1763 (2000).
Gao et al. "Structure and functional expression of the human macrophage inflammatory protein 1α/RANTES receptor" J. Exp. Med. 177:1421-1427 (1993).
Gao et al. "Human cytomegalovirus open reading frame US28 encodes a functional β chemokine receptor" J. Bio Chem. 269:28539-28542 (1994).
George et al. "Current methods in sequence comparison and analysis" Macromolecular Sequencing and Synthesis Selected Methods and Applications, Alan Liss Inc., New York, pp. 127-149 (1988).
Graham et al. "Identification and Characterization of an Inhibitor of haemopoietic stem cell proliferation" Nature 344:442-444. (1990).
Kawasaki et al. "Intervention of thymus and activation-regulated chemokine attenuates the development of allergic airway inflammation and hyperresponsive in mice" J. Immunol. 166:2055-2062 (2001).
Libert et al. "Selective amplification and cloning of four new members of the G protein-coupled receptor family" Science 244:569-572 (1989).
Neote et al. "Molecular cloning, functional characteristics of a CC chemokine receptor" Cell 72:415-425 (1993).
Panina-Bordignon et al. "The C-C chemokine receptors CCR4 and CCR8 identify airway T cells of allergen-challenged atopic asthmatics" J. Clin. Invest. 107:1357-1364 (2001).
Yamagami et al. "cDNA cloning and functional expression of a human monocyte chemoattractant protein 1 receptor" Biochem. Biophy. Res. Comm. 202:1156-1162 (1994).
Power et al. "Molecular cloning and functional expression of a novel CC chemokine receptor cDNA from a huma basophilic cell line" J. Biol. Chem. 270:19495-19500 (1995).

(Continued)

Primary Examiner—Christine J Saoud
Assistant Examiner—Fozia M Hamud
(74) Attorney, Agent, or Firm—Elizabeth J. Hecht; William T. Han

(57) ABSTRACT

A chemokine receptor binds to MCP-1, MIP-1α and/or RANTES. It can be used in screening for agents which act as antagonists to MCP-1, MIP-1α and/or RANTES. Such agents may be useful in treating various disorders, including allergies, atheromas and diseases mediated by viruses. They may also be useful in preventing graft rejection and in protecting stem cells from potentially damaging effects of chemotherapy.

5 Claims, 7 Drawing Sheets

OTHER PUBLICATIONS

Int'l Search Report for PCT/GB96/00143 May 10, 1996.
Hoogewerf et al. "Molecular cloning of murine CC CKR-4 and high affinity binding of chemokines to murine and human CC CKR-4" Biochem.Biophys. Res. Comm. 218:337-343 (1996).
Horuk et al. "Molecular properties of the chemokine receptor family" TiPS 15:159-165 (1994).
Imai et al. "Molecular cloning of a novel T cell-directed CC chemokine expressed in thymus by signal sequence trap using Epstein-Barr virus vector" J. Biol. Chem. 271:21514-21521 (1996).
Imai et al. "The T cell-directed CC chemokine TARC is a highly specific biological ligand for CC chemokine receptor 4" J. Biol. Chem. 272:15036-15042 (1997).
Imai et al. "Macrophage-derived chemokine is a functional ligand for the CC chemokine receptor 4" J. Biol. Chem. 273:1764-1768 (1998).
Jones et al. "Replacing the complementarity-determining regions in a human antibody with those from a mouse" Nature 321:522-525 (1986).
Kelvin et al. "Chemokines and serpentines: The molecular biology of chemokine receptors" J. Leukocyte Biol. 54:604-612 (1993).
Riechmann et al. "Reshaping human antibodies for therapy" Nature 332:323-327 (1988).
Reiss et al. "CC chemokine receptor (CCR)4 and the CCR10 ligand cutaneous T cell-attracting chemokine (CTACK) in lymphocyte trafficking to inflamed skin" J. Exp. Med. 194:1541-1547 (2001).
Barnes "New drugs for asthma" Nature Rev. 3:831-844 (2004).
Blom et al. Characterization of a human basophil-like cell line (LAMA-84) Scand. J. Immunol. 44:54-61 (1996).
Dahinden et al. "Monocyte chemotactic protein 3 is a most effective basophil- and eosinophil-activating chemokine" J. Exp. Med. 179:751-756 (1994).
Hulme et al. "Strategy and tactics in receptor-binding studies" in *Receptor-Ligand Interactions*, Hulme (ed.), Oxford Univ. Press, Chapter 4, pp. 63-175 (1992).
Iellem et al. "Unique chemotactic response profile and specific expression of chemokine receptors CCR4 and CCR8 by CD4$^+$CD25$^+$ regulatory T cells" J. Exp. Med. 194:847-853 (2001).

Juremalm et al. "Selective CCL5/RANTES-induced mast cell migration through interactions with chemokine receptors CCR1 and CCR4" Biochem. Biophys. Res. Comm. 297:480-485 (2002).
Rang et al. "How drugs act: General principles" in Pharmacology, $2^{nd}$ Ed., Churchill Livingstone, Chapter 1, pp. 3-23 (1991).
Elliott et al. "Treatment of rheumatoid arthritis with chimeric monoclonal antibodies to tumor necrosis factor α" Arth. & Rheumat. 36:1681-1690 (1993).
Gear et al. "Adenosine diphosphate strongly potentiates the ability of the chemokines MDC, TARC, and SDF-1 to stimulate platelet function" Blood 97:937-945 (2001).
Hopkin "Can super-antibody drugs be tamed?" Nature 440:855-856 (2006).
Jopling et al. "The identification, characterization, and distribution of guinea pig CCR4 and epitope mapping of a blocking antibody" J. Biol. Chem. 277:6864-6873 (2002).
Kawano et al. "Synthesis and biological evaluation of 2,4-diaminoquinazoline derivatives and related compounds as novel CC chemokine receptor 4 (CCR4) antagonists" MEDI abstract 376 at the $234^{th}$ ACS National Meeting, Boston, MA (Jul. 25, 2007) three pages.
Niwa et al. "Defucosylated chimeric anti-CC chemokine receptor 4 IgG1 with enhanced antibody-dependent cellular cytotoxicity shows potent therapeutic activity to T-cell leukemia and lymphoma" Cancer Res. 64:2127-2133 (2004).
Presta "Selection, design, and engineering of therapeutic antibodies" J. Allergy Clin. Immunol. 116:731-736 (2005).
Purandare et al. "Antagonists of CCR4 as Immunomodulatory Agents" Curr. Topics Medicinal Chem. 6:1335-1344 (2006).
Ravensberg et al. "The effect of a single inhaled dose of a VLA-4 antagonist on allergen-induced airway responses and airway inflammation in patients with asthma" Allergy 61:1097-1103 (2006).
Scrip "Kyowa's anti-allergy antibody shows first signs of efficacy" PJB Publications Ltd. (Jul. 26, 2007).

* cited by examiner

FIG. 1 cDNA sequence and deduced amino acid sequence of clone TM(2-7)5.5

```
  1 GGTATCTGCCGATAGTGCACGCGGTGTTTTCCTTGAGGGCAAGGACCTTGACTTATGGGG   60
      Y  L  A  I  V  H  A  V  F  S  L  R  A  R  T  L  T  Y  G  V
 61 TCATCACCAGTTTGGCTACATGGTCAGTGGCTGTGTTCGCCTCCCTTCCTGGCTTTCTGT  120
      I  T  S  L  A  T  W  S  V  A  V  F  A  S  L  P  G  F  L  F
121 TCAGCACTTGTTATACTGAGCGCAACCATACCTACTGCAAAACCAAGTACTCTCTCAACT  180
      S  T  C  Y  T  E  R  N  H  T  Y  C  K  T  K  Y  S  L  N  S
181 CCACGACGTGGAAGGTTCTCAGCTCCCTGGAAANCAACATTCTCGGATTGGTGATCCCCT  240
      T  T  W  K  V  L  S  S  L  E  X  N  I  L  G  L  V  I  P  L
241 TAGGGATCATGCTGTTTTGCTACTCCATGATCATCAGGACCTTGCAGCATTGTAAAAATG  300
      G  I  M  L  F  C  Y  S  M  I  I  R  T  L  Q  H  C  K  N  E
301 AGAAGAAGAACAAGGCGGTGAAGATGATCTTTGCCGTGGTGGTCCTCTTCCTTGGGTTCT  360
      K  K  N  K  A  V  K  M  I  F  A  V  V  V  L  F  L  G  F  W
361 GGACACCTTACAACATAGTGCTCTTCCTAGAGACCCTGGTGGAGCTAGAAGTCCTTCAGG  420
      T  P  Y  N  I  V  L  F  L  E  T  L  V  E  L  E  V  L  Q  D
421 ACTGCACCTTTGAAAGATACTTGGACTATGCCAGCCAGGCCACAGAAACTCTGGCTTTTG  480
      C  T  F  E  R  Y  L  D  Y  A  S  Q  A  T  E  T  L  A  F  V
481 TTCACTGCTGCCTCAATCCCCTCCTCTACGCCGT  514
      G  C  C  L  N  P  L  L  Y  A
```

FIG. 2

Oligonucleotide primers used to determine the full sequence of E1-C19

```
K5-5AS   5' AGA GTA CTT GGT TTT GCA GTA G        (ANTISENSE)

K5-5AS2  5' GCA GCA GTG AAC AAA AGC CAG          (ANTISENSE)

K5-5A    5' CAT AGT GCT CTT CCT AGA GAC          (SENSE)

K5-5B    5' GGT TGA GCA GGT ACA CAT CAG          (ANTISENSE)

K5-5C    5' CAA TAC TGT GGG CTC CTC C            (SENSE)

K5-5D    5' GCT CAG GTC CAT GAC TG               (SENSE)

K5-5E    5' CTC ATG AGC ATT GAT AG               (SENSE)

K5-5F    5' CTG AGC GCA ACC ATA CC               (SENSE)

K5-5G    5' GCT AGA AGT CCT TCA GG               (SENSE)

K5-5H    5' GGA TCA TGA TCT TCA TG               (SENSE)

K5-5FLA  5' AAA TGA AAC CCC ACG GAT ATA GCAG     (SENSE)

K5-5FLB  5' TCC TAC AGA GCA TCA TGA AGA TC       (ANTISENSE)
```

FIG 3A
cDNA sequence and deduced amino acid sequence of K5.5

| | |
|---|---:|
| cgggggtttt catcttcttc cccttctttt cttccccttc ttctttcctt cctccctccc | 60 |
| tctctcattt cccttctcct tctccctcag tctccacatt caacattgac aagtccattc | 120 |
| agaaaagcaa gctgcttctg gttgggccca gacctgcctt gaggagcctg tagagttaaa | 180 |
| aa atg aac ccc acg gat ata gca gat acc acc ctc gat gaa agc ata | 227 |
|     Met Asn Pro Thr Asp Ile Ala Asp Thr Thr Leu Asp Glu Ser Ile | |
| | |
| tac agc aat tac tat ctg tat gaa agt atc ccc aag cct tgc acc aaa | 275 |
| Tyr Ser Asn Tyr Tyr Leu Tyr Glu Ser Ile Pro Lys Pro Cys Thr Lys | |
| | |
| gaa ggc atc aag gca ttt ggg gag ctc ttc ctg ccc cca ctg tat tcc | 323 |
| Glu Gly Ile Lys Ala Phe Gly Glu Leu Phe Leu Pro Pro Leu Tyr Ser | |
| | |
| ttg gtt ttt gta ttt ggt ctg ctt gga aat tct gtg gtg gtt ctg gtc | 371 |
| Leu Val Phe Val Phe Gly Leu Leu Gly Asn Ser Val Val Val Leu Val | |
| | |
| ctg ttc aaa tac aag cgg ctc agg tcc atg act gat gtg tac ctg ctc | 419 |
| Leu Phe Lys Tyr Lys Arg Leu Arg Ser Met Thr Asp Val Tyr Leu Leu | |
| | |
| aac ctt gcc atc tcg gat ctg ctc ttc gtg ttt tcc ctc cct ttt tgg | 467 |
| Asn Leu Ala Ile Ser Asp Leu Leu Phe Val Phe Ser Leu Pro Phe Trp | |
| | |
|  ggc tac tat gca gca gac cag tgg gtt ttt ggg cta ggt ctg tgc aag | 515 |
| Gly Tyr Tyr Ala Ala Asp Gln Trp Val Phe Gly Leu Gly Leu Cys Lys | |
| | |
| atg att tcc tgg atg tac ttg gtg ggc ttt tac agt ggc ata ttc ttt | 563 |
| Met Ile Ser Trp Met Tyr Leu Val Gly Phe Tyr Ser Gly Ile Phe Phe | |
| | |
| gtc atg ctc atg agc att gat aga tac ctg gcg ata gtg cac gcg gtg | 611 |
| Val Met Leu Met Ser Ile Asp Arg Tyr Leu Ala Ile Val His Ala Val | |
| | |
| ttt tcc ttg agg gca agg acc ttg act tat ggg gtc atc acc agt ttg | 659 |
| Phe Ser Leu Arg Ala Arg Thr Leu Thr Tyr Gly Val Ile Thr Ser Leu | |
| | |
| gct aca tgg tca gtg gct gtg ttc gcc tcc ctt cct ggc ttt ctg ttc | 707 |
| Ala Thr Trp Ser Val Ala Val Phe Ala Ser Leu Pro Gly Phe Leu Phe | |
| | |
| agc act tgt tat act gag cgc aac cat acc tac tgc aaa acc aag tac | 755 |
| Ser Thr Cys Tyr Thr Glu Arg Asn His Thr Tyr Cys Lys Thr Lys Tyr | |

FIG 3B
cDNA sequence and deduced amino acid sequence of K5.5

| | |
|---|---:|
| tct ctc aac tcc acg acg tgg aag gtt ctc agc tcc ctg gaa atc aac<br>Ser Leu Asn Ser Thr Thr Trp Lys Val Leu Ser Ser Leu Glu Ile Asn | 803 |
| att ctc gga ttg gtg atc ccc tta ggg atc atg ctg ttt tgc tac tcc<br>Ile Leu Gly Leu Val Ile Pro Leu Gly Ile Met Leu Phe Cys Tyr Ser | 851 |
| atg atc atc agg acc ttg cag cat tgt aaa aat gag aag aag aac aag<br>Met Ile Ile Arg Thr Leu Gln His Cys Lys Asn Glu Lys Lys Asn Lys | 899 |
| gcg gtg aag atg atc ttt gcc gtg gtg gtc ctc ttc ctt ggg ttc tgg<br>Ala Val Lys Met Ile Phe Ala Val Val Val Leu Phe Leu Gly Phe Trp | 947 |
| aca cct tac aac ata gtg ctc ttc cta gag acc ctg gtg gag cta gaa<br>Thr Pro Tyr Asn Ile Val Leu Phe Leu Glu Thr Leu Val Glu Leu Glu | 995 |
| gtc ctt cag gac tgc acc ttt gaa aga tac ttg gac tat gcc atc cag<br>Val Leu Gln Asp Cys Thr Phe Glu Arg Tyr Leu Asp Tyr Ala Ile Gln | 1043 |
| gcc aca gaa act ctg gct ttt gtt cac tgc tgc ctt aat ccc atc atc<br>Ala Thr Glu Thr Leu Ala Phe Val His Cys Cys Leu Asn Pro Ile Ile | 1091 |
| tac ttt ttt ctg ggg gag aaa ttt cgc aag tac atc cta cag ctc ttc<br>Tyr Phe Phe Leu Gly Glu Lys Phe Arg Lys Tyr Ile Leu Gln Leu Phe | 1139 |
| aaa acc tgc agg ggc ctt ttt gtg ctc tgc caa tac tgt ggg ctc ctc<br>Lys Thr Cys Arg Gly Leu Phe Val Leu Cys Gln Tyr Cys Gly Leu Leu | 1187 |
| caa att tac tct gct gac acc ccc agc tca tct tac acg cag tcc acc<br>Gln Ile Tyr Ser Ala Asp Thr Pro Ser Ser Ser Tyr Thr Gln Ser Thr | 1235 |
| atg gat cat gat ctc cat gat gct ctg tagaaaaatg aaatggtgaa<br>Met Asp His Asp Leu His Asp Ala Leu | 1282 |
| atgcagagtc aatgaacttt tccacattca gagcttactt taaaattggt attttaggt | 1342 |
| aagagatccc tgagccagtg gtcaggagga aaggcttaca cccacaggtg ggaaagacag | 1402 |
| gttctcatcc ctgcaggnag gtttttcttc tccccactta ganaaagtnc caggcctgga | 1462 |
| aggggtccaa cccngggttg aggatccttc ccccaaaccc agggtttggc ctggaggatt | 1522 |
| aatncaaaan ntttnttgaa actcttgaan angttgngnt aagtttnggg gggttntttt | 1582 |
| gaaggnaagt ttttcccttc ttncc | 1607 |

FIG. 4

Northern blot analysis of K5.5 expression in peripheral tissues

| TISSUE | K5.5 |
|---|---|
| HEART | - |
| BRAIN | - |
| PLACENTA | - |
| LUNG | - |
| LIVER | - |
| SKELETAL MUSCLE | - |
| KIDNEY | - |
| PANCREAS | - |
| SPLEEN | ++ |
| THYMUS | +++ |
| PROSTATE | - |
| TESTIS | +/- |
| OVARY | - |
| SMALL INTESTINE | +/- |
| COLON | - |
| PERIPHERAL BLOOD LEUKOCYTES | +++ |

FIG. 5

Expression of K5.5 receptor mRNA peripheral blood T cell populations and some T cell lines.

| T CELL / T CELL LINES | K5.5 |
|---|---|
| T CELLS + IL-2 (4h) | ++ |
| T CELLS + IL-2 (12h) | ++ |
| T CELLS + IL-2 (24h) | ++ |
| T CELLS + IL-2 (48h) | ++ |
| T CELLS + IL-2 (72h) | ++ |
| T CELLS + IL-2 (7 DAYS) | ++ |
| T CELLS + PMA (2 DAYS) | ++ |
| JURKAT | + |
| MOLT-4 | +/- |
| T CELLS (UNSTIMULATED) | + |
| CD8 + T CELL CLONE | + |
| T8 CLONE | +++ |
| T8 + GH | +++ |
| T8 + GR | - |
| T8 + Giα | + |
| T4 CLONE | +++ |
| TT20 (IL2 STIMULATED) | ++ |
| CD45 RO | - |
| CD45 RO (STIMULATED) | - |
| CD45 RA | - |
| CD45 RA (STIMULATED) | - |
| HUT 78 | - |
| HUT 78 (STIMULATED) | - |

FIG. 6

Expression of K5.5 receptor mRNA in non-T leukocytes and cell lines

| NON-T CELL LEUKOCYTES / LINES | K5.5 |
|---|---|
| PERIPHERAL BLOOD B CELLS | + |
| B CELLS (ACTIVATED) | |
| RAJI | - |
| GCC (TONSIL) | - |
| GCC (ANTI CD40 MAb) | - |
| BL2 LINE | - |
| RPMI 8666 | - |
| KU812 | ++ |
| EOL-3 LINE | +/- |
| MACROPHAGES (ALVEOLAR) | - |
| MIXED LUNG LEUKOCYTES | +/- |
| MONOCYTES | - |
| HMC-1 LINE | - |

FIG. 7

Analysis of K5.5 receptor mRNA expression by RT-PCR in human cell lines and peripheral blood leukocyte populations

Current induced in voltage clamped oocytes on stimulation with different chemokine ligands (1μM) at 2 min intervals (results of individual oocytes tested are shown).

SEQUENCE LISTING

<160> NUMBER OF SEQ ID NOS: 20

<210> SEQ ID NO 1
<211> LENGTH: 8
<212> TYPE: PRT
<213> ORGANISM: Homo Sapien

<400> SEQUENCE: 1

Arg Tyr Leu Ala Ile Val His Ala
 1               5

<210> SEQ ID NO 2
<211> LENGTH: 9
<212> TYPE: PRT
<213> ORGANISM: Homo sapien
<220> FEATURE:
<221> NAME/KEY: VARIANT
<222> LOCATION: 2
<223> OTHER INFORMATION: Xaa = Leu, Val, or Ile
<220> FEATURE:
<221> NAME/KEY: VARIANT
<222> LOCATION: 5
<223> OTHER INFORMATION: Xaa = Ile, Leu, Met, or Val
<220> FEATURE:
<221> NAME/KEY: VARIANT
<222> LOCATION: 6
<223> OTHER INFORMATION: Xaa = Ile or Leu
<220> FEATURE:
<221> NAME/KEY: VARIANT
<222> LOCATION: 8
<223> OTHER INFORMATION: Xaa = Ala or Val
<220> FEATURE:
<221> NAME/KEY: VARIANT
<222> LOCATION: 9
<223> OTHER INFORMATION: Xaa = Phe or Val

<400> SEQUENCE: 2

Cys Xaa Asn Pro Xaa Xaa Tyr Xaa Xaa
 1               5

<210> SEQ ID NO 3
<211> LENGTH: 22
<212> TYPE: PRT
<213> ORGANISM: Homo sapien

<400> SEQUENCE: 3

Gly Ile Thr Ala Tyr Tyr Thr Ile Gly Cys Ile Ala Thr His Gly Thr
 1               5                  10                  15

Ile Cys Ala Tyr Gly Cys
            20

<210> SEQ ID NO 4
<211> LENGTH: 25
<212> TYPE: PRT
<213> ORGANISM: Homo sapien

<400> SEQUENCE: 4

Ala Met Ile Arg Cys Arg Thr Ala Ile Ala Asp Ile Ala Ile Ile Gly
 1               5                  10                  15

Gly Arg Thr Thr Ile Ala Ile Arg Cys
            20                  25

<210> SEQ ID NO 5
<211> LENGTH: 514
<212> TYPE: DNA
<213> ORGANISM: Homo sapien

```
<220> FEATURE:
<221> NAME/KEY: CDS
<222> LOCATION: (3)...(512)
<220> FEATURE:
<221> NAME/KEY: misc_feature
<222> LOCATION: 214
<223> OTHER INFORMATION: n = A,T,C or G

<400> SEQUENCE: 5 gg tat ctg gcg ata gtg cac gcg gtg ttt tcc ttg agg gca agg acc       47
   Tyr Leu Ala Ile Val His Ala Val Phe Ser Leu Arg Ala Arg Thr
    1               5                  10                  15 ttg act tat ggg gtc atc acc agt ttg gct aca tgg tca gtg gct gtg      95
Leu Thr Tyr Gly Val Ile Thr Ser Leu Ala Thr Trp Ser Val Ala Val
                20                  25                  30 ttc gcc tcc ctt cct ggc ttt ctg ttc agc act tgt tat act gag cgc     143
Phe Ala Ser Leu Pro Gly Phe Leu Phe Ser Thr Cys Tyr Thr Glu Arg
            35                  40                  45 aac cat acc tac tgc aaa acc aag tac tct ctc aac tcc acg acg tgg     191
Asn His Thr Tyr Cys Lys Thr Lys Tyr Ser Leu Asn Ser Thr Thr Trp
        50                  55                  60 aag gtt ctc agc tcc ctg gaa anc aac att ctc gga ttg gtg atc ccc     239
Lys Val Leu Ser Ser Leu Glu Xaa Asn Ile Leu Gly Leu Val Ile Pro
    65                  70                  75 tta ggg atc atg ctg ttt tgc tac tcc atg atc atc agg acc ttg cag     287
Leu Gly Ile Met Leu Phe Cys Tyr Ser Met Ile Ile Arg Thr Leu Gln
 80                  85                  90                  95 cat tgt aaa aat gag aag aag aac aag gcg gtg aag atg atc ttt gcc     335
His Cys Lys Asn Glu Lys Lys Asn Lys Ala Val Lys Met Ile Phe Ala
                100                 105                 110 gtg gtg gtc ctc ttc ctt ggg ttc tgg aca cct tac aac ata gtg ctc     383
Val Val Val Leu Phe Leu Gly Phe Trp Thr Pro Tyr Asn Ile Val Leu
            115                 120                 125 ttc cta gag acc ctg gtg gag cta gaa gtc ctt cag gac tgc acc ttt     431
Phe Leu Glu Thr Leu Val Glu Leu Glu Val Leu Gln Asp Cys Thr Phe
        130                 135                 140 gaa aga tac ttg gac tat gcc agc cag gcc aca gaa act ctg gct ttt     479
Glu Arg Tyr Leu Asp Tyr Ala Ser Gln Ala Thr Glu Thr Leu Ala Phe
    145                 150                 155 gtt cac tgc tgc ctc aat ccc ctc ctc tac gcc gt                       514
Val His Cys Cys Leu Asn Pro Leu Leu Tyr Ala
160                 165                 170

<210> SEQ ID NO 6
<211> LENGTH: 170
<212> TYPE: PRT
<213> ORGANISM: Homo sapien
<220> FEATURE:
<221> NAME/KEY: VARIANT
<222> LOCATION: 71
<223> OTHER INFORMATION: Xaa = Any Amino Acid

<400> SEQUENCE: 6

Tyr Leu Ala Ile Val His Ala Val Phe Ser Leu Arg Ala Arg Thr Leu
 1               5                  10                  15

Thr Tyr Gly Val Ile Thr Ser Leu Ala Thr Trp Ser Val Ala Val Phe
                20                  25                  30

Ala Ser Leu Pro Gly Phe Leu Phe Ser Thr Cys Tyr Thr Glu Arg Asn
            35                  40                  45

His Thr Tyr Cys Lys Thr Lys Tyr Ser Leu Asn Ser Thr Thr Trp Lys
        50                  55                  60

Val Leu Ser Ser Leu Glu Xaa Asn Ile Leu Gly Leu Val Ile Pro Leu
```

-continued

```
                65                  70                  75                  80
Gly Ile Met Leu Phe Cys Tyr Ser Met Ile Arg Thr Leu Gln His
                    85                  90                  95
Cys Lys Asn Glu Lys Lys Asn Lys Ala Val Lys Met Ile Phe Ala Val
                100                 105                 110
Val Val Leu Phe Leu Gly Phe Trp Thr Pro Tyr Asn Ile Val Leu Phe
                115                 120                 125
Leu Glu Thr Leu Val Glu Leu Val Leu Gln Asp Cys Thr Phe Glu
            130                 135                 140
Arg Tyr Leu Asp Tyr Ala Ser Gln Ala Thr Glu Thr Leu Ala Phe Val
145                 150                 155                 160
His Cys Cys Leu Asn Pro Leu Leu Tyr Ala
                165                 170

<210> SEQ ID NO 7
<211> LENGTH: 22
<212> TYPE: DNA
<213> ORGANISM: Homo sapien

<400> SEQUENCE: 7
agagtacttg gttttgcagt ag                                                22

<210> SEQ ID NO 8
<211> LENGTH: 21
<212> TYPE: DNA
<213> ORGANISM: Homo sapien

<400> SEQUENCE: 8
gcagcagtga acaaaagcca g                                                 21

<210> SEQ ID NO 9
<211> LENGTH: 21
<212> TYPE: DNA
<213> ORGANISM: Homo sapien

<400> SEQUENCE: 9
catagtgctc ttcctagaga c                                                 21

<210> SEQ ID NO 10
<211> LENGTH: 21
<212> TYPE: DNA
<213> ORGANISM: Homo sapien

<400> SEQUENCE: 10
ggttgagcag gtacacatca g                                                 21

<210> SEQ ID NO 11
<211> LENGTH: 19
<212> TYPE: DNA
<213> ORGANISM: Homo sapien

<400> SEQUENCE: 11
caatactgtg ggctcctcc                                                    19

<210> SEQ ID NO 12
<211> LENGTH: 17
<212> TYPE: DNA
<213> ORGANISM: Homo sapien

<400> SEQUENCE: 12
gctcaggtcc atgactg                                                      17
```

<210> SEQ ID NO 13
<211> LENGTH: 17
<212> TYPE: DNA
<213> ORGANISM: Homo sapien

<400> SEQUENCE: 13
ctcatgagca ttgatag                                                   17

<210> SEQ ID NO 14
<211> LENGTH: 17
<212> TYPE: DNA
<213> ORGANISM: Homo sapien

<400> SEQUENCE: 14
ctgagcgcaa ccatacc                                                   17

<210> SEQ ID NO 15
<211> LENGTH: 17
<212> TYPE: DNA
<213> ORGANISM: Homo sapien

<400> SEQUENCE: 15
gctagaagtc cttcagg                                                   17

<210> SEQ ID NO 16
<211> LENGTH: 17
<212> TYPE: DNA
<213> ORGANISM: Homo sapien

<400> SEQUENCE: 16
ggatcatgat cttcatg                                                   17

<210> SEQ ID NO 17
<211> LENGTH: 25
<212> TYPE: DNA
<213> ORGANISM: Homo sapien

<400> SEQUENCE: 17
aaatgaaacc ccacggatat agcag                                          25

<210> SEQ ID NO 18
<211> LENGTH: 23
<212> TYPE: DNA
<213> ORGANISM: Homo sapien

<400> SEQUENCE: 18
tcctacagag catcatgaag atc                                            23

<210> SEQ ID NO 19
<211> LENGTH: 1607
<212> TYPE: DNA
<213> ORGANISM: Homo sapien
<220> FEATURE:
<221> NAME/KEY: CDS
<222> LOCATION: (183)...(1262)
<220> FEATURE:
<221> NAME/KEY: misc_feature
<222> LOCATION: 1420, 1445, 1451, 1476, 1526, 1532, 1533, 1537, 1552,
      1554, 1559, 1561, 1569, 1578, 1588, 1605
<223> OTHER INFORMATION: n = A,T,C or G

<400> SEQUENCE: 19
cgggggtttt catcttcttc cccttctttt cttcccttc ttctttcctt cctccctccc    60

-continued

```
tctctcattt cccttctcct tctccctcag tctccacatt caacattgac aagtccattc      120
agaaaagcaa gctgcttctg gttgggccca gacctgcctt gaggagcctg tagagttaaa      180 aa atg aac ccc acg gat ata gca gat acc acc ctc gat gaa agc ata        227
   Met Asn Pro Thr Asp Ile Ala Asp Thr Thr Leu Asp Glu Ser Ile
   1               5                  10                  15 tac agc aat tac tat ctg tat gaa agt atc ccc aag cct tgc acc aaa       275
Tyr Ser Asn Tyr Tyr Leu Tyr Glu Ser Ile Pro Lys Pro Cys Thr Lys
                20                  25                  30 gaa ggc atc aag gca ttt ggg gag ctc ttc ctg ccc cca ctg tat tcc       323
Glu Gly Ile Lys Ala Phe Gly Glu Leu Phe Leu Pro Pro Leu Tyr Ser
            35                  40                  45 ttg gtt ttt gta ttt ggt ctg ctt gga aat tct gtg gtg gtt ctg gtc       371
Leu Val Phe Val Phe Gly Leu Leu Gly Asn Ser Val Val Val Leu Val
        50                  55                  60 ctg ttc aaa tac aag cgg ctc agg tcc atg act gat gtg tac ctg ctc       419
Leu Phe Lys Tyr Lys Arg Leu Arg Ser Met Thr Asp Val Tyr Leu Leu
    65                  70                  75 aac ctt gcc atc tcg gat ctg ctc ttc gtg ttt tcc ctc cct ttt tgg       467
Asn Leu Ala Ile Ser Asp Leu Leu Phe Val Phe Ser Leu Pro Phe Trp
80                  85                  90                  95 ggc tac tat gca gca gac cag tgg gtt ttt ggg cta ggt ctg tgc aag       515
Gly Tyr Tyr Ala Ala Asp Gln Trp Val Phe Gly Leu Gly Leu Cys Lys
                100                 105                 110 atg att tcc tgg atg tac ttg gtg ggc ttt tac agt ggc ata ttc ttt       563
Met Ile Ser Trp Met Tyr Leu Val Gly Phe Tyr Ser Gly Ile Phe Phe
            115                 120                 125 gtc atg ctc atg agc att gat aga tac ctg gcg ata gtg cac gcg gtg       611
Val Met Leu Met Ser Ile Asp Arg Tyr Leu Ala Ile Val His Ala Val
        130                 135                 140 ttt tcc ttg agg gca agg acc ttg act tat ggg gtc atc acc agt ttg       659
Phe Ser Leu Arg Ala Arg Thr Leu Thr Tyr Gly Val Ile Thr Ser Leu
    145                 150                 155 gct aca tgg tca gtg gct gtg ttc gcc tcc ctt cct ggc ttt ctg ttc       707
Ala Thr Trp Ser Val Ala Val Phe Ala Ser Leu Pro Gly Phe Leu Phe
160                 165                 170                 175 agc act tgt tat act gag cgc aac cat acc tac tgc aaa acc aag tac       755
Ser Thr Cys Tyr Thr Glu Arg Asn His Thr Tyr Cys Lys Thr Lys Tyr
                180                 185                 190 tct ctc aac tcc acg acg tgg aag gtt ctc agc tcc ctg gaa atc aac       803
Ser Leu Asn Ser Thr Thr Trp Lys Val Leu Ser Ser Leu Glu Ile Asn
            195                 200                 205 att ctc gga ttg gtg atc ccc tta ggg atc atg ctg ttt tgc tac tcc       851
Ile Leu Gly Leu Val Ile Pro Leu Gly Ile Met Leu Phe Cys Tyr Ser
        210                 215                 220 atg atc atc agg acc ttg cag cat tgt aaa aat gag aag aag aac aag       899
Met Ile Ile Arg Thr Leu Gln His Cys Lys Asn Glu Lys Lys Asn Lys
    225                 230                 235 gcg gtg aag atg atc ttt gcc gtg gtg gtc ctc ttc ctt ggg ttc tgg       947
Ala Val Lys Met Ile Phe Ala Val Val Val Leu Phe Leu Gly Phe Trp
240                 245                 250                 255 aca cct tac aac ata gtg ctc ttc cta gag acc ctg gtg gag cta gaa       995
Thr Pro Tyr Asn Ile Val Leu Phe Leu Glu Thr Leu Val Glu Leu Glu
                260                 265                 270 gtc ctt cag gac tgc acc ttt gaa aga tac ttg gac tat gcc atc cag      1043
Val Leu Gln Asp Cys Thr Phe Glu Arg Tyr Leu Asp Tyr Ala Ile Gln
            275                 280                 285 gcc aca gaa act ctg gct ttt gtt cac tgc tgc ctt aat ccc atc atc      1091
Ala Thr Glu Thr Leu Ala Phe Val His Cys Cys Leu Asn Pro Ile Ile
        290                 295                 300
```

```
tac ttt ttt ctg ggg gag aaa ttt cgc aag tac atc cta cag ctc ttc      1139
Tyr Phe Phe Leu Gly Glu Lys Phe Arg Lys Tyr Ile Leu Gln Leu Phe
305                 310                 315 aaa acc tgc agg ggc ctt ttt gtg ctc tgc caa tac tgt ggg ctc ctc      1187
Lys Thr Cys Arg Gly Leu Phe Val Leu Cys Gln Tyr Cys Gly Leu Leu
320                 325                 330                 335 caa att tac tct gct gac acc ccc agc tca tct tac acg cag tcc acc      1235
Gln Ile Tyr Ser Ala Asp Thr Pro Ser Ser Ser Tyr Thr Gln Ser Thr
                340                 345                 350 atg gat cat gat ctc cat gat gct ctg tagaaaaatg aaatggtgaa            1282
Met Asp His Asp Leu His Asp Ala Leu
                355                 360 atgcagagtc aatgaacttt tccacattca gagcttactt taaaattggt atttttaggt    1342
aagagatccc tgagccagtg gtcaggagga aaggcttaca cccacaggtg ggaaagacag    1402
gttctcatcc ctgcaggnag gttttttcttc tccccactta ganaaagtnc caggcctgga   1462
aggggtccaa cccngggttg aggatccttc ccccaaaccc agggtttggc ctggaggatt    1522
aatncaaaan ntttnttgaa actcttgaan angttgngnt aagtttnggg gggttntttt    1582
gaaggnaagt ttttcccttc ttncc                                          1607
```

<210> SEQ ID NO 20
<211> LENGTH: 360
<212> TYPE: PRT
<213> ORGANISM: Homo sapien

<400> SEQUENCE: 20

```
Met Asn Pro Thr Asp Ile Ala Asp Thr Thr Leu Asp Glu Ser Ile Tyr
1               5                   10                  15

Ser Asn Tyr Tyr Leu Tyr Glu Ser Ile Pro Lys Pro Cys Thr Lys Glu
                20                  25                  30

Gly Ile Lys Ala Phe Gly Glu Leu Phe Leu Pro Pro Leu Tyr Ser Leu
            35                  40                  45

Val Phe Val Phe Gly Leu Leu Gly Asn Ser Val Val Val Leu Val Leu
    50                  55                  60

Phe Lys Tyr Lys Arg Leu Arg Ser Met Thr Asp Val Tyr Leu Leu Asn
65                  70                  75                  80

Leu Ala Ile Ser Asp Leu Leu Phe Val Phe Ser Leu Pro Phe Trp Gly
                85                  90                  95

Tyr Tyr Ala Ala Asp Gln Trp Val Phe Gly Leu Gly Leu Cys Lys Met
            100                 105                 110

Ile Ser Trp Met Tyr Leu Val Gly Phe Tyr Ser Gly Ile Phe Phe Val
        115                 120                 125

Met Leu Met Ser Ile Asp Arg Tyr Leu Ala Ile Val His Ala Val Phe
    130                 135                 140

Ser Leu Arg Ala Arg Thr Leu Thr Tyr Gly Val Ile Thr Ser Leu Ala
145                 150                 155                 160

Thr Trp Ser Val Ala Val Phe Ala Ser Leu Pro Gly Phe Leu Phe Ser
                165                 170                 175

Thr Cys Tyr Thr Glu Arg Asn His Thr Tyr Cys Lys Thr Lys Tyr Ser
            180                 185                 190

Leu Asn Ser Thr Thr Trp Lys Val Leu Ser Ser Leu Glu Ile Asn Ile
        195                 200                 205

Leu Gly Leu Val Ile Pro Leu Gly Ile Met Leu Phe Cys Tyr Ser Met
    210                 215                 220
```

-continued

```
Ile Ile Arg Thr Leu Gln His Cys Lys Asn Glu Lys Lys Asn Lys Ala
225                 230                 235                 240

Val Lys Met Ile Phe Ala Val Val Val Leu Phe Leu Gly Phe Trp Thr
            245                 250                 255

Pro Tyr Asn Ile Val Leu Phe Leu Glu Thr Leu Val Glu Leu Glu Val
        260                 265                 270

Leu Gln Asp Cys Thr Phe Glu Arg Tyr Leu Asp Tyr Ala Ile Gln Ala
        275                 280                 285

Thr Glu Thr Leu Ala Phe Val His Cys Cys Leu Asn Pro Ile Ile Tyr
    290                 295                 300

Phe Phe Leu Gly Glu Lys Phe Arg Lys Tyr Ile Leu Gln Leu Phe Lys
305                 310                 315                 320

Thr Cys Arg Gly Leu Phe Val Leu Cys Gln Tyr Cys Gly Leu Leu Gln
            325                 330                 335

Ile Tyr Ser Ala Asp Thr Pro Ser Ser Ser Tyr Thr Gln Ser Thr Met
            340                 345                 350

Asp His Asp Leu His Asp Ala Leu
            355             360
```

USES OF A CHEMOKINE RECEPTOR ABLE TO BIND TO MCP-1, MIP-1α AND/OR RANTES

This application is a continuation of application Ser. No. 09/764,413, filed Jan. 19, 2001, now U.S. Pat. No. 6,919,432; which is a continuation of application Ser. No. 09/614,256, filed Jul. 12, 2000, abandoned: which is a continuation of application Ser. No. 08/875,573, filed Oct. 31, 1997, now U.S. Pat. No. 6,150,132: which is a national-phase filed under 35 U.S.C. 371 of Int'l Appln. No. PCT/GB96/00143, filed Jan. 24, 1996; the entire contents of which is hereby incorporated by reference in this application.

FIELD OF THE INVENTION

The present invention relates to chemokine receptors.

BACKGROUND OF THE INVENTION

Chemokines are a growing family of chemotactic cytokines, which have been implicated to play a role in the recruitment and activation of cells (Oppenheim, J. J. et al., Ann Rev Immunol., 9 617-48, (1991), Schall, T. J., Cytokine, 3 165-183, (1991)). They are primarily responsible for the activation and recruitment of leukocytes, but not exclusively so. Further analysis of this superfamily of proteins has shown that it can be divided up into two further subfamilies of proteins. These have been termed CXC or α-chemokines, and the CC or β-chemokines based on the spacings of two conserved cysteine residues near to the amino terminus of the proteins.

To date two receptors have been identified for the CC chemokine family. The first, which is receptor primarily for MIP-1α (Macrophage inflammatory polypeptide-1α) and RANTES (Raised on Activation, Normal T-cell derived and Secreted) has been described previously (Gao, J. L. et al., J. Exp. Med., 177 1421-7 (1993), Neote, K. et al., Cell 72 415-25 (1993)). The second CC-chemokine receptor which has been recently described is for MCP-1 (monocyte chemotractant protein-1) Charo I. et al., Proc. Natl. Acad. Sci. USA 91 2752-2756 (1994). More recently, another receptor US28, expressed by the human cytomegalovirus, has been shown to be a receptor for RANTES, MIP-1α, and MCP-1 (Gao, J. L. and Murphy P. M., J. Biol. Chem. 269, 28539-28542 (1994)). All three receptors are of the seven transmembrane alpha helical segment type, and are expressed into the membranes of cells.

However there remains a need to identify hitherto undisclosed chemokine receptors and to characterise them in order to develop a more complete picture of the structure and function of chemokine receptors.

BRIEF SUMMARY OF THE INVENTION

According to the present invention there is provided a chemokine receptor having the amino acid sequence shown in FIG. 3.

This receptor is preferably capable of binding MCP-1, MIP-1α and RANTES. It may be important in basophil and T-cell function.

It can be used to screen for pharmaceutically active agents. The present invention therefore includes within its scope such agents (which may or may not be proteins). They may be provided in a pharmaceutical composition together with a pharmaceutically acceptable carrier.

Such a composition is within the scope of the present invention. It may be prepared by admixing the carrier with the pharmaceutically active agent under sterile conditions. The pharmaceutical composition may be provided in unit dosage form. It may be present as part of a kit including instructions for use.

The pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route.

A receptor of the present invention can be used to screen for agents useful in treating allergies e.g. asthma, atopic dermatitis, rhinitis, hay fever, eczema or food allergies. It may also be useful in screening for agents useful in treating conjunctivitis. MCP-1, MIP-1α and RANTES all bind to the receptor of the present invention and are capable of causing histamine release from basophils. An agent which blocks this binding may thereby prevent or reduce the release of histamine from basophils (i.e. act antagonistically to MCP-1, MIP-1α or RANTES). Such agents may be variants of MCP-1, MIP-1α or RANTES (in which one or more amino acids are deleted, substituted or inserted relative to MCP-1, MIP-1α or RANTES), although this is not essential.

It may also be involved in the activation of T-lymphocytes, a common characteristic of immune and other inflammatory states.

The binding of agents to the receptor of the present invention can be assayed by suitable techniques.

For example, electrophysiological techniques may be used. In one such technique, a *Xenopus* oocyte, for example, can be used to express a receptor of the present invention. The receptor can be expressed on the oocyte membrane following micro-injection into the oocyte of RNA coding for said receptor.

When a ligand binds to the receptor, it can cause a release of calcium ions either from intracellular stores, or from extracellular sources. These calcium fluxes then cause a chloride current across the cell membrane which can be measured electrophysiologically.

Such currents are discussed in Wahlestedt, C., Ann. N.Y. Acad. Sci. 632 116-22 (1991) and Boton, R et al., J. Physiol. (London) 408 511-534 (1989), for example.

As an alternative to using electrophysiological techniques or other techniques which rely upon a biological response to receptor binding, more direct assays of binding can be used. Thus ligands could be labelled with a detectable label, allowed to bind to a receptor, and the label could then be detected. Suitable labels which could be used include radiolabels, fluorescent labels, enzymes which can cause a detectable change, etc.

The receptor of the present invention may also be used to screen for agents suitable for treating atheromas. In this regard it should be noted that MCP-1 is a key recruiter of monocytes to atherosclerotic plagues. The receptor can be used to screen for agents which prevent or reduce such recruitment (act antagonistically to MCP-1α). Such agents may be variants of MCP-1 itself (wherein one or more amino acids are deleted, substituted or inserted relative to MCP-1), although this is not essential.

A further use of the receptor of the present invention is to screen for agents which cause inhibition of stem cell proliferation, in other words to screen for agonists of MIP-1α. MIP-1α has been shown (Graham, G. J. et al., Nature 344 442-(1990)) to inhibit proliferation of hemopoietic stem cell proliferation. As such, receptor agonists could be used to prevent stem cell proliferation during chemotherapy, which would therefore protect the stem cells from the potentially damaging effects of such chemotherapy.

MIP-1α is known to be a stem cell proliferation inhibitor and agents which are also stem cell proliferation inhibitors can be screened using the receptor of the present invention. Such agents may be variants of MIP-1α itself (wherein one or more amino acids are deleted, substituted or inserted relative to MIP-1α), although this is not essential.

Another use of the receptor of the present invention is in screening for agents useful in reducing the likelihood of transplant rejection or in increasing the length of time before rejection occurs. High levels of RANTES are sometimes found in renal grafts and may be associated with the rejection of such grafts. Agents which prevent or reduce the binding of RANTES to the receptor of the present invention may therefore be useful in transplantation by acting antagonistically to RANTES. Such agents may be variants of RANTES itself (wherein one or more amino acids are deleted, substituted or inserted relative to RANTES), although this is not essential.

A further use of the present invention is in screening for substances useful in treating diseases mediated by viruses. Thus it may be used as a screen for antiviral agents.

One example of this is in screening for agents useful in treating AIDS. MIP-1α and RANTES levels have been suggested as being at least partially responsible for certain AIDS patients surviving longer than others. Since a receptor of the present invention may bind to MIP-1α and/or RANTES, it can be used for screening for other agents which could be useful in treating AIDS.

It is also notable that Human Cytomegalovirus and Herpes viruses have chemokine receptors. The present invention could be used to screen for agents useful in treating diseases mediated by such viruses.

It should be noted that the present invention is not limited to the receptor having the amino acids sequence shown in FIG. 3 but that it covers variants (allelic and non-allelic variants) having one or more amino acid deletions, insertions or substitutions relative to said sequence, provided that said variants are capable of binding to at least one of the chemokines: RANTES, MIP-1α and MCP-1. (Desirably, however, the receptors are capable of binding to all of these chemokines). Binding may be determined by monitoring the response of cells in electrophysiological assay using oocytes, as already described.

For example, it will be appreciated by the skilled person that various amino acids may often be substituted for other amino acids which have similar properties without substantially altering or adversely affecting certain properties of a protein. Thus the amino acids glycine, valine, leucine or isoleucine can often be substituted for one another (amino acids having aliphatic hydroxyl side chains). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains) and cysteine and methionine (amino acids having sulphur containing side chains). Thus the present invention includes within its scope variants of the receptor shown in FIG. 3 which includes one or more such substitutions.

It is however preferred that variants of the receptor having the amino acid sequence shown in FIG. 3 have substantial amino acid identity with said amino acid sequence. The degree of amino acid identity can be calculated using a program such as "bestfit" (Smith and Waterman, Advances in Applied Mathematics, 482-489 (1981)) to find the best segment of similarity between the two sequences. The alignment is based on maximising the score achieved using a matrix of amino acid similarities, such as that described by Schwarz and Dayhof (1979) Atlas of Protein Sequence and Structure, Dayhof, M. O., Ed pp 353-358.

Preferably however the degree of sequence identity is at least 50% or at least 60%, and more preferably it is above 75%. Sequence identities of at least 80%, e.g. at least 90% or at least 95%, are most preferred.

The receptor or variant thereof may include an N-terminal methionine. Such methionines are sometimes incorporated during translation and not subsequently removed.

The receptor or variant may be covalently linked to another moiety (e.g. a protein). Thus fusion proteins may be formed. These are well known in the art and may be used to assist in identification or purification or to otherwise alter the properties of the receptor of a variant thereof (e.g. to alter its stability and/or is binding properties).

Truncated variants of the receptor having the amino acid sequence shown in FIG. 3 may also be provided since one or more amino acids may be deleted from said sequence, whilst retaining binding to MIP-1α, RANTES and/or MCP-1. These may be N-terminal deletions, C-terminal deletions or may occur within said sequence.

The receptor or variant (of whatever nature) may be provided in substantially pure form. It may be isolated from other proteins and may be isolated from a cell membrane. It may be in glycosylated or unglycosylated form (depending upon the expression system used). A receptor or variant thereof of the present invention may be provided by any appropriate technique.

Gene cloning techniques are preferably used. Such techniques are disclosed, for example, in J. Sambrook et al., *Molecular Cloning* 2nd Edition, Cold Spring Harbor Laboratory Press (1989).

Alternatively, chemical synthesis may be used (although this is less preferred). For example, short synthetic peptides may be prepared and then linked together to provide a substance of the present invention. Such peptides can be prepared by techniques known to those skilled in the art. Thus one end of a molecule can be immobilised and desired amino acid residue can be added sequentially. Protective groups can be used to avoid undesired side-reactions and may then be removed.

Variants of the receptor of the present invention together with the receptor itself are referred to below as substances of the present invention.

Such substances can be used in raising or selecting antibodies. The present invention therefore includes antibodies which bind to a substance of the present invention. Preferred antibodies bind specifically to substances of the present invention so that they can be used to purify such substances. The antibodies may be monoclonal or polyclonal.

Polyclonal antibodies can be raised by stimulating their production in a suitable animal host (e.g. a mouse, rat, guinea pig, rabbit, sheep, goat or monkey) when the substance of the present invention is injected into the animal. If necessary an adjuvant may be administered together with the substance of the present invention. The antibodies can then be purified by virtue of their binding to a substance of the present invention.

Monoclonal antibodies can be produced from hybridomas. These can be formed by fusing myeloma cells and spleen cells which produce the desired antibody in order to form an immortal cell line. This is the well known Kohler & Milstein technique (*Nature* 256 52-55 (1975)).

Techniques for producing monoclonal and polyclonal antibodies which bind to a particular protein are now well developed in the art. They are discussed in standard immunology textbooks, for example in Roitt et al, *Immunology* second edition (1989), Churchill Livingstone, London.

In addition to whole antibodies, the present invention includes derivatives thereof which are capable of binding to substances of the present invention.

Thus the present invention includes antibody fragments and synthetic constructs. Examples of antibody fragments and synthetic constructs are given by Dougall et al in *Tibtech* 12 372-379 (September 1994).

Antibody fragments include, for example, Fab, F(ab')$_2$ and Fv fragments (see Roitt et al [supra]).

Fv fragments can be modified to produce a synthetic construct known as a single chain Fv (scFv) molecule. This includes a peptide linker covalently joining V$_h$ and V$_l$ regions which contribute to the stability of the molecule.

Other synthetic constructs include CDR peptides. These are synthetic peptides comprising antigen binding determinants. Peptide mimetics may also be used. These molecules are usually conformationally restricted organic rings which mimic the structure of a CDR loop and which include antigen-interactive side chains.

Synthetic constructs include chimaeric molecules. Thus, for example, humanised (or primatised) antibodies or derivatives thereof are within the scope of the present invention. An example of a humanised antibody is an antibody having human framework regions, but rodent hypervariable regions.

Synthetic constructs also include molecules comprising a covalently linked moiety which provides the molecule with some desirable property in addition to antigen binding. For example the moiety may be a label (e.g. a fluorescent or radioactive label) or a pharmaceutically active agent.

The antibodies or derivatives thereof of the present invention have a wide variety of uses. They can be used in purification and/or identification of the substances of the present invention. Thus they may be used in diagnosis.

They can be provided in the form of a kit for screening for the substances of the present invention.

The present invention also includes within its scope nucleic acid molecules coding for substances of the present invention (i.e. for the aforesaid receptor or variants thereof). The nucleic acid molecules may be RNA or DNA and may be provided in isolated or recombinant form.

Nucleic acid molecules of the present invention may be provided by any appropriate technique.

Gene cloning techniques are preferred (see Sambrook et al, supra). Variants of a given nucleic acid sequence can be prepared by mutagenesis techniques (e.g. site directed mutagenesis).

Chemical synthesis techniques can alternatively be used, but are less preferred.

Vectors may be used to incorporate the nucleic acid molecules of the present invention. The vectors may be eukaryotic or prokaryotic vectors and may be incorporated into appropriate host cells or into non-cellular expression systems.

Nucleic acid molecules which are complementary to the aforesaid nucleic acid molecules are also within the scope of the present invention. These are sometimes referred to as "antisense molecules". They can hybridise to complementary nucleic acid molecules and may thereby prevent or reduce the expression of a gene product. Thus they can be used to alter gene expression.

The use of such molecules is useful in studying gene function and regulation. Appropriate labelling and hybridisation techniques can be useful to identify the location of coding regions.

The present invention also includes within its scope nucleic acids which can be used as probes for chemokine receptors. Preferred probes can hybridise specifically to a nucleic acid coding for the protein having the amino acid sequences given in FIG. 3, or for variants thereof, as described above. Such probes can be of any suitable length, but would typically be above 15 nucleotides long and may be at least 100 nucleotides long Desirably probes will hybridise to a target sequence under stringent hybridisation conditions. An example of stringent hybridisation conditions is a temperature of 35°-65° C. and a salt concentration of about 0.9 molar. Other stringent hybridisation conditions may be used and the salt concentration need not be as high as 0.9 molar.

The nucleic acid sequences given in FIGS. 1 and 3 herein or fragments thereof can be used as probes or primers or to prepare probes or primers.

The primers may be used to amplify nucleic acid sequences e.g. by using PCR or other amplification techniques. The probes may be used in diagnosis or in purification.

DETAILED DESCRIPTION OF THE INVENTION

The present invention will now be explained by way of example only, with reference to the accompanying drawings, wherein:

BRIEF DESCRIPTION OF THE DRAWINGS

FIG. 1 shows a cDNA sequence (SEQ ID NO:5) and a deduced amino acid sequence (SEQ ID NO:6) of a clone designated "TM(2-7)5.5", which was used to probe a human spleen λGT11 cDNA library.

FIG. 2 shows various primers (SEQ ID NOS:7-18), respectively which were used in sequencing a clone isolated from the library referred to in respect of FIG. 1 above by using the TM(2-7)5.5 DNA as a probe.

FIGS. 3A and 3B show the cDNA sequence and the deduced amino acid sequence in respect of the clone referred to in respect of FIG. 2 above, the clone being designated "K5.5".

FIGS. 4 to 6 show Northern Blot analyses prepared using TM(2-7)5.5 DNA in various hybridisation studies. In these figures the following scoring system is used:

+++ Very strong positive signal visible after four hours' exposure of the autoradiograph.

++ Clear positive signal visible after four hours' exposure of the autoradiograph.

+ Signal not visible after four hours' exposure of the autoradiograph, but clear after 24 hours.

+/− Weak positive signal only visible after 24 hours' exposure.

− No signal.

Probes were used at a specific activity of $10^6$ cpm/ml hybridisation solution.

FIG. 7 shows on agarose gels an analysis of K5.5 receptor mRNA expression products from leukocytes and some human cell lines, RNA having been amplified using reverse transcriptase PCR.

Figure 8A:
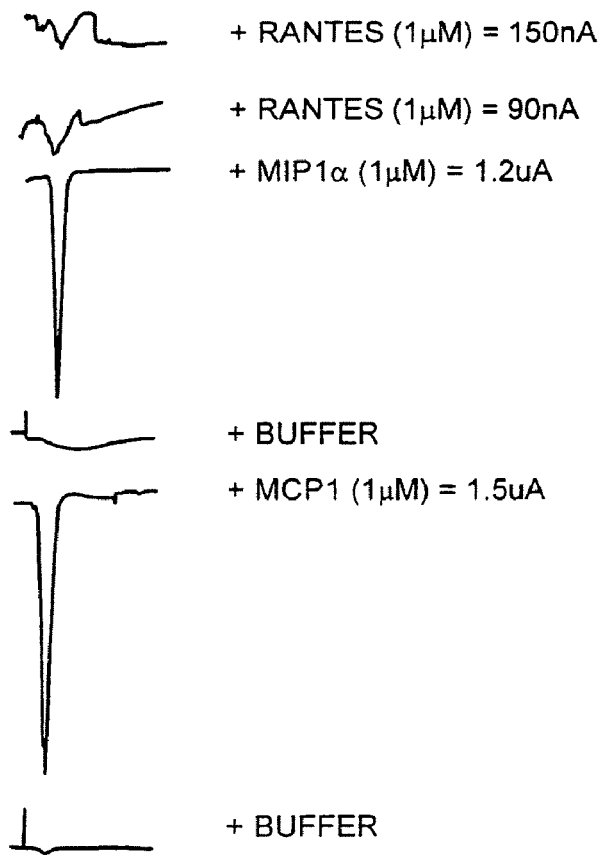

FIG. 8A shows an analysis of the current induced in voltage clamped *Xenopus* oocytes, into which K5.5 cRNA had been micro-injected, on stimulation with various chemokine ligands.

Figure 8B:
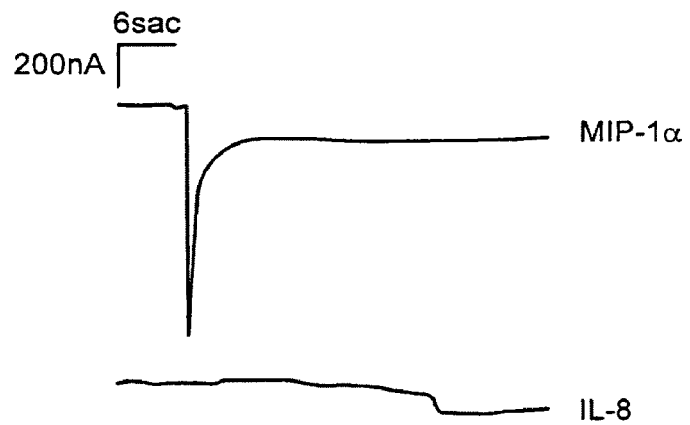

FIG. 8B shows an analysis similar to that performed in respect of FIG. 8A but using different chemokines (apart from MIP-1α, which is shown in both figures for comparison). The present inventors were unable to obtain any data showing that IL-8 binds to CC-CKR3 molecules. Preferred receptors within the scope of the present invention do not bind to IL-8.

Figure 9:
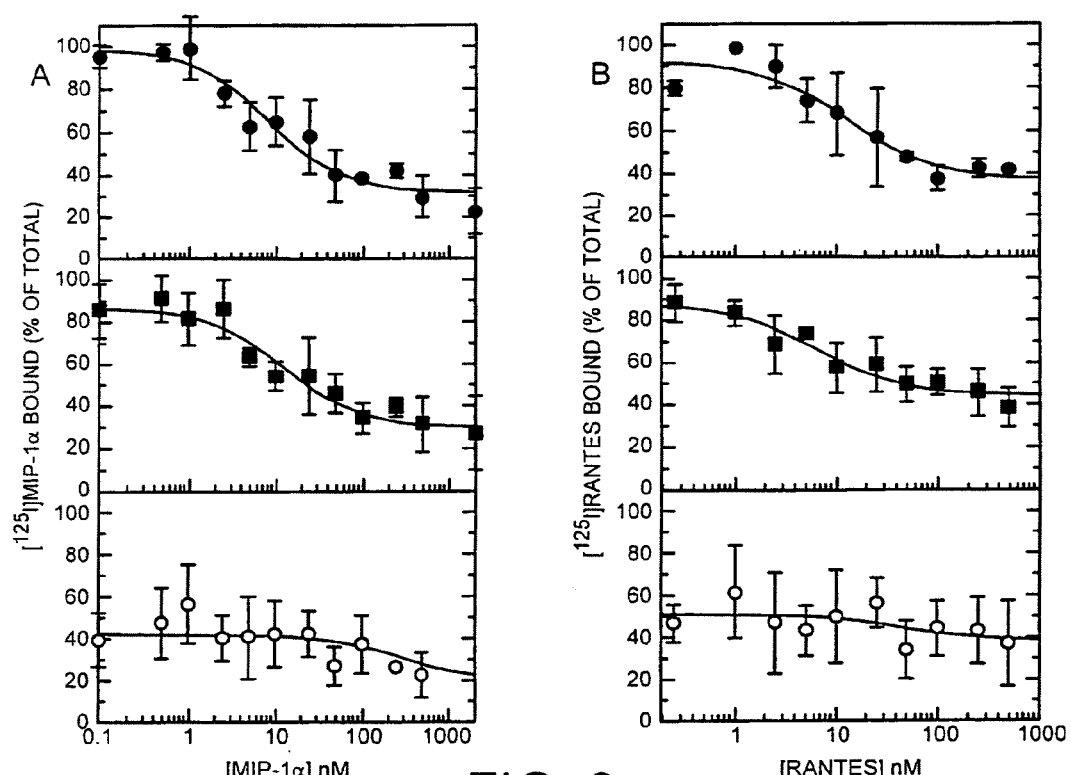

FIG. 9 shows the results of a binding assay using [$^{125}$I] MIP-1α and [$^{125}$I] RANTES to bind to human and murine CC-CKR-3 molecules.

EXAMPLES

An alignment of the amino acid sequences of IL-S receptor A and B and of the C-C CKR-1 (MIP-1α/RANTES receptor) indicated that a region between proposed transmembrane domains 3 and 4 contains the conserved amino acid sequence RYLAIVHA (SEQ ID NO:1).

A second conserved amino acid sequence occurs in the proposed 7th transmembrane domain in these three receptors as well as in two non-chemokine chemotactic peptide receptors for fMLP (formyl-methionine-leucinephenylalanine) and CSa as follows (SEQ ID NO:2):

C L (or V, I) N P I (or L,M,V) I (or L) Y A (or V) F (or V)

Degenerate oligonucleotides were prepared containing the majority of possible codons which could be translated to give the above-mentioned amino acid sequences.

These oligonucleotides had the sequences (SEQ ID NOS:3 and 4):

a) sense 5' GIT AYY TIG CIA THG TIC AYG C or b) antisense 5' AMI RCR TAI ADI AII GGR TTI AIR C using the IUB/GCG codes, wherein
I=inosine which can substitute for A, T, G, or C
Y=C or T
H=A, C or T
M=A or C
R=A or G
D=A, G or T The oligonucleotides were then used to clone a human CC chemokine receptor using the procedure set out below.

(a) Cloning of a Sequence Designated Human K5.5 (CC-CKR-3)*

(*The designation CC-CKR-3 is used here for consistency with the designation used in the priority document. However it is noted that other research groups are now using the designation CC-CKR-3 for a different molecule and that the molecule referred to herein as CC-CKR-3 may now be referred to in the literature as CC-CKR-4.)

Total RNA was isolated from 1×10$^8$ KU812 cells by the method of Chomczynski and Sacchi, (1987) (Single-step method of RNA isolation by acid guanidinium thiocyanate-phenol-chloroform extraction, Anal. Biochem. 162 156-159). These cells were from a human basophilic KU812 cell line which was a gift of Dr K Kishi, Niigata, Japan.

PolyA+mRNA was subsequently isolated by oligodT cellulose chromatography using a polyA quik mRNA purification kit (Stratagene). Single-stranded cDNA was prepared from 1 μg of polyA+mRNA in a 50 μl reaction containing 1 μg oligodT$_{12-18}$, 4 mM methyl mercuric hydroxide, 1 mM dNTPs, 50 mM Tris-HCl pH 8.3 buffer, 50 mM KCl, 8 mM MgCl$_2$, 10 units RNAsin and 100 units of AMV reverse transcriptase-XL (Life Sciences Inc.) for 60 mm at 42° C. 5 μl aliquots of the reaction mixture were then subjected to 40 cycles of PCR (95° C. 2 mm; 37° C., 2 mm and 72° C., 2 mm) in 10 mM Tris-HCl pH 8.3 buffer, 50 mM KCl, 1.5 mM MgCl$_2$, 0.2 mM dNTPS and 2.5 units of Amplitaq™ (Perkin Elmer Cetus) using 3 μM of each degenerate oligonucleotide primer (SEQ ID NOS:3 and 4) (sense 5' GIT AYY TIG CIA THG TIC AYG C and antisense 5' AMI RCR TAI ADI All GGR TTI AIR C) in a Techne PHC-2 thermal cycler.

PCR reaction products were visualized on 1% agarose gels containing 0.5 μg/ml ethidium bromide. Reaction products migrating at the predicted size (500-550 bp) were gel purified by standard methods (Sambrook J. et al., 1989 in Molecular Cloning: A Laboratory Manual. Cold Spring Harbor Laboratory Press. Cold Spring Harbor, N.Y.). Gel purified DNA was then rendered blunt-ended by sequential treatment with T4 polynucleotide kinase (New England Biolabs) according to the manufacturer's instructions, in a total volume of 50 μl for 1 h at 37° C. After this time, 2.5 μl of 2.5 mM dNTPs and 1 μl of E. coli DNA polymerase I Klenow fragment (New England Biolabs) were added and the incubation continued for a further 30 min at 37° C. The reaction mixture was then heat inactivated at 70° C. for 30 min and then extracted once with Tris-HCl pH 8.0 saturated phenol/chloroform (1:1 v/v). DNA was precipitated by addition of 10 μl 3M sodium acetate pH 5.5, 1 μl glycogen (20 mg/ml) (Boehringer) and 250 μl ethanol at −20° C. The DNA was recovered by centrifugation at 10 000×g for 20 min at 4° C. and washed with 70% ethanol. The final pellet was resuspended in sterile water at a concentration of 10 ng/μl.

A pBluescript II SK-cloning vector (Stratagene) was prepared as follows: 20 μg of CsCl gradient purified plasmid was digested in a reaction volume of 100 μl for 2 h at 37° C. with 200 units of Eco RV or Eco RI (New England Biolabs) according to the manufacturer's instructions. After 2 h, the digested vector was treated with 10 μl of calf intestinal alkaline phosphatase (20 units/ml) (Boehringer) for a further 30 min at 37° C.

The reaction mixture was inactivated by heating at 68° C. for 15 min and then extracted once with Tris-HCl pH 8.0 saturated phenol/chloroform (1:1 v/v). Plasmid DNA was precipitated by addition of 10 μl 3M sodium acetate pH 5.5 and 250 μl ethanol at −20° C. The DNA was recovered by centrifugation at 10 000×g for 20 min at 4° C., washed with 70% ethanol. The final pellet was resuspended in sterile water at a concentration of 50 ng/ml.

Blunt-ended PCR product (10 ng) was ligated to 50 ng of Eco RV digested, alkaline phosphatase treated pBluescript II SK-plasmid cloning vector in a 20 μl volume using 2 μl of T4 DNA ligase (400 000 units/ml) (New England Biolabs) for at least 16 h at 15° C. Ligation products were diluted to 100 μl with 1×TE (10 mM Tris-HCl pH 8.0/1 mM EDTA) and phenol/chloroform extracted as described previously. Ligation products were precipitated by the addition of 10 μl 3M sodium acetate pH 5.5, 1 μl glycogen (20 mg/ml) and 250 μl ethanol for 15 min at −70° C. DNA was recovered by centrifugation as described above and resuspended in 10 μl of sterile water. Five μl of resuspended ligation products were then electroporated into electrocompetent E. coli strain XL-1 blue (recA1, endA1, gyrA96, thi-1, hsdR17, supE44, relA1, lac, {F' proAB, lacIqZDM15, Tn10 (tet$^r$)} (40 μl) using a Bio Rad Gene pulser according to the manufacturer's instructions. Following electroporation, 1 ml of LB medium was added and cells were grown at 37° C. for 1 h. After this time, 100 μl aliquots of the culture medium were plated on LB plates containing 100 μg/ml of ampicillin and grown up for 16 h at 37° C. Individual bacterial colonies were then picked into 5 ml of LB medium containing 100 μg/ml of ampicillin and grown overnight at 37° C. Small scale plasmid DNA preparations (mini-preps) were then made from 3 ml of each culture using a Wizard™ mini-prep DNA purification system (Promega) according to the manufacturer's instructions. Three μl aliquots of mini-prep DNA was then digested with restriction enzymes Hind III and Eco RI (both from New England Biolabs) according to the manufacturer's instructions in a reaction volume of 15 μl. Reaction products were analysed on 1% agarose gels containing 0.5 μg/ml ethidium bromide. Mini-prep DNAs which yielded an insert size of approximately 500-550 bp were then subjected to DNA sequence analysis using T3 and T7 primers and Sequenase (USB) according to the manufacturer's instructions.

A comparison of the sequences obtained against the GenBank/EMBL/DDBJ databases revealed that 10/23 sequences analysed showed 60% identity at the DNA level to the human C-C CKR-1 (MIP-1α/RANTES receptor) (Neote et al., Molecular cloning, functional expression and signalling characteristics of a C-C chemokine receptor, Cell 72 415-425 (1993)). The sequence of one of the clones designated TM(2-7)5.5 (shortened to K5.5) is shown in FIG. 1.

CsCl gradient-purified plasmid DNA was prepared for clone K5.5 by standard methods. 20 μg of plasmid DNA was digested at 37° C. with restriction enzymes Hind III and Eco RI according to the manufacturer's instructions (New England Biolabs). Digestion products were analysed on 1% agarose gels containing 0.5 μg/ml ethidium bromide. The 514 bp insert DNA corresponding to the sequenced PCR product was gel purified as described previously. One hundred ng of the 514 bp insert was labelled with $^{32}$P-dCTP (Amersham International) using a random-primed DNA-labelling kit (Boehringer) according to the manufacturer's instructions, and used to screen 5×10$^5$ clones of a human spleen λGT11 cDNA library (Clontech) according to the manufacturer's instructions. Following hybridization, duplicating positives were rescreened with the same probe until a pure positive phage plaque was obtained. Phage DNA was recovered from positive plaques using standard methods (Sambrook J. et al (1989)). Purified phage DNA (100 μg) was digested with 200 units of Eco RI (New England Biolabs) in buffer 2 (New England Biolabs) for 16 h at 37° C. Digestion products were fractionated on 1% agarose gels containing ethidium bromide (0.5 μg/ml) and cDNA inserts were gel purified and ligated into the Eco RI site of pBluescript II SK-vector as described above. Ligation products were transformed into *E. coli* strain XL-1 blue (recA1, endA1, gyrA96, thi-1, hsdR17, supE44, relA1, lac, {F' proAB, lacIqZDM15, Tn10 (tet$^r$)] by electroporation as previously. Individual, ampicillin resistant bacterial colonies were inoculated into L-Broth containing 100 μg/ml ampicillin and grown up for 16 h at 37° C. Mini-prep DNA was prepared from 3 ml of overnight culture medium as described above. Three μl aliquots of mini-prep DNA was then digested with restriction enzyme Eco RI according to the manufacturers' instructions in a reaction volume of 15 μl. Reaction products were analysed on 1% agarose gels containing 0.5 μg/ml ethidium bromide. Mini-preps which contained cDNA inserts were subsequently sequenced using Sequenase™ and T3 and T7 primers on an Applied Biosystems DNA sequencer.

One clone designated E1-C19, was shown by sequencing with the T7 primer to contain the putative 5' end of K5.5. CsCl gradient-purified DNA of clone E1-C19 was subsequently resequenced with T3 and T7 primers and several internal sequencing primers based on the previous sequencing results (primer sequences are shown in FIG. 2). The sequence of E1-C19 insert cDNA is shown in FIG. 3.

(b) Northern Blot Analysis

Multiple tissue Northern blots were purchased from Clontech and hybridized to the 514 bp Hind III/Eco RI fragment of pTM(2-7)5.5 according to the manufacturer's instructions. For other Northern blots, total RNA was prepared from cell lines and peripheral blood leukocyte populations by the method of Chomczynski and Sacchi (1987). All of the cell lines used in this study were maintained in RPMI 1640 medium containing 10% heat inactivated FCS and 50 μg/ml gentamycin (all purchased from Gibco-BRL). Total peripheral blood mononuclear cells and polymorphonuclear cells were purified by density gradient centrifugation on Ficoll (Pharmacia). Leukocytes were sorted by FACS using the appropriately labelled antibody on a FACS star (Becton Dickinson) to obtain pure populations (>90%) of B cells (CD20), T cells (CD4, CD8, CD45R0, CD45RA) and monocytes (CD14). Pulmonary macrophages and mixed lung leukocytes were prepared from resected human lung samples using the method of Nicod et al (1989) (Separation of potent and poorly functional human lung accessory cells based on autofluorescence. J. Leukocyte. Biol. 45 458).

5 μg of each RNA was electrophoresed in 1% agarose gels containing 2.2% (v/v) formaldehyde, transferred to nitrocellulose and probed with the $^{32}$P-dCTP labelled 514 bp insert from TM(2-7)5.5 using standard Northern blot procedure (Sambrook et al (1989)). The results are shown in FIGS. 4 to 6.

(c) Analysis of K5.5 Receptor mRNA Expression in Leukocytes and Some Human Cell Lines by Reverse Transcriptase PCR 10 μg of total RNA (in a volume of 10 μl) and 0.5 μl of 0.5 mg/ml solution of oligodT$_{15}$ were heated at 70° C. for 10 min and then cooled on ice for 2 min, followed by addition of 4 μl of 5×1st strand buffer, 2 μl of 0.1 M DTT, 1 μl of 10 mM dNTPs and 1 μl Superscript™ for 1 h at 37° C. All reagents for the reverse transcription (RT) reaction were from Gibco-BRL except oligodT$_{15}$ (Stratagene). Two μl aliquots of each RT reaction was then subjected to 40 cycles of PCR (2 min 95° C.; 2 min, 55° C. and 2 min, 72° C.) in a 100 μl reaction mixture containing 100 pmoles each of primers K5-5FLA and K5-5FLB. PCR reaction products (10 μl) were analysed on 1% agarose gels as described above, for the presence of a 1085 bp reaction product corresponding to the full coding sequence of K5.5. The results are shown in FIG. 7, wherein the samples in the lanes indicated in FIG. 7 are as follows:

| Lane | Sample |
| --- | --- |
| 1 | Molecular weight markers (1 kb ladder) |
| 2 | PB T cells (IL-2 stimulated) |
| 3 | PB T cells |
| 4 | Jurkat |
| 5 | MOLT-4 |
| 6 | PB B cells |
| 7 | PB B cells |
| 8 | pulmonary macrophages |
| 9 | PB monocytes |
| 10 | KU812 |
| 11 | EOL-3 |
| 12 | SW900 (lung epithelial cell line) |
| 13 | CCLu32 (lung fibroblast cell line) |
| 14 | LL24 (lung fibroblast cell line) |
| 15 | AALT.16 (aortic smooth muscle cell line) |

(d) Expression of K5.5 cRNA in *Xenopus* oocytes

CsCl-gradient purified pE1-C19 plasmid DNA (5 μg) was linearized using restriction enzyme Bam HI (New England Biolabs) in a 100 µl reaction volume overnight at 37° C. Linearized plasmids were treated with 2 µl of proteinase K (16.7 mg/ml Boehringer) for 30 min at 37° C. DNA was extracted twice with phenol (0.1 M Tris-saturated pH 8.0) and once with chloroform. Glycogen (1 µl of 20 mg/ml stock solution) was added to the aqueous phase and linearized DNA was precipitated following addition of 0.1 volume of 3 M sodium acetate pH 5.5 and 2.5 volumes of ethanol for 1 h at −80° C. The DNA was recovered by centrifugation (14 000 rpm, 4° C. in a microfuge), washed with 70% ethanol and dissolved in RNase free water at 250 ng/ml.

Capped cRNA transcripts were generated from 1 µg of Bam HI (New England Biolabs) linearized DNA in a 100 µl reaction volume containing 20 µl transcription buffer (5×), 4 µl NTP mix (10 mM ATP, UTP and CTP, 3 mM GTP), 4 µl 0.75M DTT, 2.5 µl RNAsin, 0.5 µl GTP (10 mM), 4 µl CAP analog (10 mM m7G(5')ppp(5')G) and 2.5 µl of T7 or T3 RNA polymerase respectively. All reagents used for the in vitro transcription reaction were from Promega except CAP analog (Pharmacia). After 1.5 h at 37° C., 4 µl RQ1 DNase (Promega) was added and the reaction mixture was incubated for a further 15 min at 37° C. The reaction mixture was extracted twice with 0.1 M Tris-HCl pH 8.0 saturated phenol/chloroform. (1:1 v/v) and once with chloroform. Glycogen (1 µl as above) was added to the aqueous phase and cRNA was precipitated overnight at −20° C. after addition of 0.1 volume, 3 M sodium acetate pH 5.5 and 2.5 volumes ethanol. cRNA was recovered by centrifugation (14 000 rpm, 4° C., 20 min in a microfuge), the pellet washed in 70% ethanol and resuspended in sterile water at 1 µg/µl. An approximate estimate of the cRNA concentration was obtained by running an aliquot of the resuspended material on a 1% agarose gel containing 2.2% (v/v) formaldehyde against RNA markers of known concentration. Samples were stored at −80° C. before use.

Oocytes were harvested from adult female *Xenopus laevis*, by standard methods (Bertrand et al., 1991). Oocytes were defolliculated by incubation in 0.2% (w/v) collagenase (Sigma) in 50 ml OR2 medium without Ca2+ and without Mg2+ in a spinner flask under slow agitation for 2 h at room temperature (OR2 medium is 82.5 mM NaCl, 2.5 mM KCl, 1 mM $Na_2HPO_4$, 15 mM HEPES, 2 mM $CaCl_2$, 1 mM $MgCl_2$ pH 7.6). Oocytes were rinsed carefully with OR2 followed by MBS (modified Barth's saline: 88 mM NaCl, 1 mM KCl, 0.33 mM $Ca(NO_3)_2$, 0.41 mM $CaCl_2$, 0.82 mM $MgSO_4$, 2.4 mM $NaHCO_3$, 10 mM HEPES, pH 7.6) and allowed to recover for at least 1-2 h in MBS before selecting stage V-VI oocytes. Selected oocytes were incubated in MBS supplemented penicillin/streptomycin (100 units/ml) (Gibco-BRL) overnight at 18° C. before injection.

Oocytes were microinjected using an Inject+Matic air pump (Gabay) using needles made from Drummond calibrated 6 ml capillaries. cRNA (25 ng in 50 nl) was injected into the cytoplasm. Oocytes were individually transferred to wells of a 96 well flat bottom culture dish and incubated in MBS for 24-72 h.

Electrophysiological recordings were made 1-3 days after injection in oocytes superfused with OR2 medium at room temperature under voltage clamped conditions using two microelectrodes (1-2 MΩ, both filled with 3 M KCl), the membrane potential being routinely clamped at −100 mV using a Gene Clamp 500 instrument (Axon).

Test chemokines were purchased from PeptroTech or produced in-house at the Glaxo Institute for Molecular Biology and resuspended at a concentration of 1 µM in PBS. Fifty µl of each chemokine was applied directly onto voltage clamped oocytes and the current induced was monitored on a Tektronix 5113 dual-beam storage oscilloscope linked to an IBM-PC. Where multiple chemokines were tested on a single oocyte, a recovery time of 2 min was allowed between each application. The results are shown in FIG. 8A.

FIG. 8B shows the results of a similar analysis to that illustrated in FIG. 8A, but using different chemokines (apart from MIP-1α).

It can be seen that no significant electrophysiological response was seen when using IL-8, in contrast with the result obtained for MIP-1α.

(e) EL-60 Cell Transfection and Ligand Binding Assay

Thirty µg human CC-CKR-3-pcDNA1neo, murine CC-CKR-3-pcDNA1neo, or pcDNA1neo were electroporated into 500 µl HL-60 cells ($2 \times 10^7$ cells/ml in 0.15 M NaCl, 20 mM HEPES, pH 7.3) using a Bio Rad Geno Pulster (260 volts, 960 µF, 0.4 cm gap cuvette). Cells were seeded into T-175 flasks containing 25 ml AIM-V serum-free media (GIBCO). On day 2 or 3 following transfection the cells were diluted in a total volume of 45 ml AIM-V media containing 600 µg/ml G418, and on day 6, cells were further diluted to 180 ml AIM-V media containing 600 µg/ml G418. On days 7-15 post-transfection cells were maintained in AIM-V media (+G418) at a density of $0.4$-$1.2 \times 10^6$ cells/ml, and binding assays were performed during this time. Equilibrium competition binding was carried out by incubating $5 \times 10_5$ cells in 100 µl binding buffer (1 mM $CaCl_2$, 5 mM $MgCl_2$, 0.5% BSA, 50 mM HEPES, pH 7.2), 0.34 nM [$^{125}$I] radioligand, and 0.5-2000 nM cold ligand in Millipore®-DV96-well filter plates. After 1.5 h incubation at room temperature, cells were washed four times by vacuum filtration with binding buffer containing 0.5 M NaCl. Fifty µl Optiphase scintillant (Wallac) were added to each well, and the radioactivity was measured with a Wallac Microbeta Plate Reader. All binding data was normalized as the percentage of total binding. Total binding for a given ligand was defined as the radioactivity bound in the absence of competing ligand to $5 \times 10^5$ cells transfected with human CC-CKR-3 (range: 1000-2500 cpm).

The results are shown in FIG. 9 which illustrates high affinity binding of [$^{125}$I]MIP-1α and [$^{125}$I]RANTES to human and murine CC-CKR-3. HL-60 cells were transfected with human CC-CKR-3 (●), murine CC-CKR-3 (■), or an empty vector (O) and maintained in AIM-V media containing G418 for 7-15 days. Equilibrium competition assays were performed as described above with [$^{125}$I]MIP-1α (A) and [$^{125}$I]RANTES (B). Each point represents the mean±S.D. of duplicate points from four (A) or three (B) separate experiments. Data were curve-fitted with GraFit 3.01 software (Leatherbarrow., R. J., GraFit Versions 3.01, Erithicus Softward Ltd., Staines, UK (1992)) using the equation $B/Bmax^{app} = 1/(1+([L]/IC_{50}))$, where B=cpm bound, $Bmax^{app}$=cpm bound in the absence of competing ligand, L=competing ligand, and the $IC_{50}$=[radioligand]+$K_d$ (Cheng., Y. and Prusoff., W. H. *Biochem Pharmacol* 22: 3099-3108 (1973)).

The invention claimed is:

1. A method of blocking the binding of a chemokine receptor comprising the amino acid sequence set forth in SEQ ID NO:20 to MCP-1, MIP-1α and/or RANTES, said method comprising the step of: contacting at least one cell that expresses said chemokine receptor with an antibody or fragment thereof that binds said chemokine receptor, thereby blocking the binding of MCP-1, MIP-1α and/or RANTES to said chemokine receptor.

2. The method according to claim 1, wherein said antibody is a monoclonal antibody.

3. The method according to claim 2, wherein said monoclonal antibody is a humanized monoclonal antibody.

4. The method according to claim 1, wherein said antibody fragment is selected from the group of: Fab, F(ab)$_2$ and FV fragments.

5. The method according to claim 4, wherein said antibody fragment is humanized.

* * * * *